(12) United States Patent
Dahmen et al.

(10) Patent No.: US 8,299,249 B2
(45) Date of Patent: *Oct. 30, 2012

(54) METHOD FOR PRODUCING TETA BY MEANS OF EDDN

(75) Inventors: Kirsten Dahmen, Freinsheim (DE); Alfred Oftring, Bad Dürkheim (DE); Katrin Baumann, Mannheim (DE); Randolf Hugo, Dirmstein (DE); Thilo Hahn, Kirchheimbolanden (DE); Johann-Peter Melder, Böhl-Iggelheim (DE)

(73) Assignee: BASF SE (DE)

( * ) Notice: Subject to any disclaimer, the term of this patent is extended or adjusted under 35 U.S.C. 154(b) by 505 days.

This patent is subject to a terminal disclaimer.

(21) Appl. No.: 12/529,072

(22) PCT Filed: Feb. 28, 2008

(86) PCT No.: PCT/EP2008/052413
§ 371 (c)(1),
(2), (4) Date: Aug. 28, 2009

(87) PCT Pub. No.: WO2008/104582
PCT Pub. Date: Sep. 4, 2008

(65) Prior Publication Data
US 2010/0121064 A1    May 13, 2010

(30) Foreign Application Priority Data

Mar. 1, 2007 (EP) .................................. 07103295

(51) Int. Cl.
*C07D 241/04* (2006.01)
*C07D 295/00* (2006.01)
(52) U.S. Cl. ........................................ 544/401; 544/402
(58) Field of Classification Search ............... 514/252.12; 544/401, 402
See application file for complete search history.

(56) References Cited

U.S. PATENT DOCUMENTS

| | | | |
|---|---|---|---|
| 3,462,493 A | 8/1969 | Coker et al. | |
| 4,146,560 A | 3/1979 | Larkin et al. | |
| 4,235,821 A | 11/1980 | Butte, Jr. et al. | |
| 4,404,167 A | 9/1983 | Rozenfeld et al. | |
| 5,030,740 A * | 7/1991 | Bowman et al. | 544/357 |
| 5,530,127 A | 6/1996 | Reif et al. | |
| 6,297,394 B1 | 10/2001 | Voit et al. | |
| 6,469,211 B2 | 10/2002 | Ansmann et al. | |
| 6,518,449 B1 | 2/2003 | Boschat et al. | |
| 6,852,669 B2 | 2/2005 | Voit et al. | |
| 7,091,153 B2 | 8/2006 | Voit et al. | |
| 7,960,591 B2 * | 6/2011 | Dahmen et al. | 564/491 |
| 2006/0041170 A1 | 2/2006 | Jonas et al. | |

FOREIGN PATENT DOCUMENTS

| | | |
|---|---|---|
| DE | 2755687 A1 | 8/1978 |
| DE | 3003729 A1 | 8/1980 |
| DE | 68911508 T2 | 3/1994 |
| EP | 0212986 A1 | 3/1987 |
| EP | 0222934 A1 | 5/1987 |
| EP | 0382508 A2 | 8/1990 |
| EP | 0696572 A1 | 2/1996 |
| EP | 0913388 A1 | 5/1999 |
| EP | 0963975 A1 | 12/1999 |
| EP | 1209146 A1 | 5/2002 |
| EP | 1742045 A1 | 1/2007 |
| WO | WO-9933561 A1 | 7/1999 |
| WO | WO-9944984 A1 | 9/1999 |

OTHER PUBLICATIONS

Nishimura, Shigeo, "Handbook of Heterogeneous Catalytic Hydrogenation for Organic Synthesis", (2001) pp. 213-215.
Malveda, Michael P., "CEH Product Review: Ethyleneamines"; SRI Report, SRI International, (2003), pp. 1-53.
Gamage, Swarna A., et al., "Dicationic Bis(9-methylphenazine-1-carboxamides): Relationships between Biological Activity and Linker Chain Structure for a Series of Potent Topoisomerase Targeted Anticancer Drugs", J. Med., Chem, (2001), vol. 44, pp. 1407-1415.
U.S. Appl. No. 12/529,101, filed Aug. 28, 2009.
U.S. Appl. No. 12/529,096, filed Aug. 28, 2009.
U.S. Appl. No. 12/529,034, filed Aug. 28, 2009.
U.S. Appl. No. 12/529,047, filed Aug. 28, 2009.
U.S. Appl. No. 12/529,079, filed Aug. 28, 2009.
U.S. Appl. No. 12/529,087, filed Aug. 28, 2009.
U.S. Appl. No. 12/529,107, filed Aug. 28, 2009.
CEH Product Review, Ethyleneamines, The Chemical Economics Handbook—SRI International, Jul. 2003.
Handbook of Heterogeneous Catalytic Hydrogenation for Organic Synthesis, Stereochemistry of the Hydrogenation of Ketones, pp. 213 and 215, (2008).
K. Masuzawa et al., Bulletin of the Chemical Society of Japan, vol. 41, 1968, pp. 702-706.
H. Baganz et al., Chem. Ber., 90, 1957, pp. 2944-2949.
H.A. Braun, et al., Helvetica Chimica Acta, vol. 43, 1960, pp. 659-666.

* cited by examiner

*Primary Examiner* — Erich A Lesser
(74) *Attorney, Agent, or Firm* — Connolly Bove Lodge & Hutz LLP

(57) ABSTRACT

The invention relates to a process for preparing triethylenetetramine (TETA), which, comprises the following steps:
a) reaction of ethylenediamine (EDA) with formaldehyde and hydrocyanic acid (HCN) in a molar ratio of EDA to formaldehyde to HCN of from 1:1.5:1.5 to 1:2:2 to give ethylenediaminediacetonitrile (EDDN),
b) hydrogenation of the EDDN obtained in step a) in the presence of a catalyst and a solvent.

23 Claims, No Drawings

METHOD FOR PRODUCING TETA BY MEANS OF EDDN

CROSS-REFERENCE TO RELATED APPLICATIONS

This application is a national stage application (under 35 U.S.C. §371) of PCT/EP2008/052413, filed Feb. 28, 2008, which claims benefit of European application 07103295.7, filed Mar. 1, 2007.

BACKGROUND OF THE INVENTION

The invention relates to a process for preparing triethylenetetramine (TETA) by hydrogenation of ethylenediaminediacetonitrile (EDDN) over a catalyst, wherein EDDN is prepared by reaction of ethylenediamine (EDA) with formaldehyde and hydrocyanic acid (HCN). If appropriate, EDDN can also be present as constituent of an amino nitrile mixture which additionally comprises ethylenediaminemonoacetonitrile (EDMN). Diethylenetriaminemonoacetonitrile (DETMN) or diethylenetriaminediacetonitrile (DETDN) can additionally be comprised in the amino nitrile mixture as a result of recirculation of diethylenetriamine (DETA) obtained, if appropriate, in the hydrogenation. Hydrogenation of these further amino nitriles additionally gives tetraethylenepentamine (TEPA).

It is generally known that aliphatic nitriles, which may optionally be additionally substituted by further functional groups, can be hydrogenated in the presence of catalysts to form the corresponding amines. As indicated below, such hydrogenation processes are also known for various amino nitriles for the purpose of preparing some amines. However, up to now it has not been disclosed anywhere that TETA can also be prepared from the amino nitrile EDDN or, if appropriate, from an amino nitrile mixture comprising EDDN and EDMN by direct hydrogenation of the amino nitrile. However, the previously known processes for preparing TETA are, as indicated below, associated with disadvantages.

The prior art describes numerous processes for the hydrogenation of the α-amino nitriles aminoacetonitrile (AAN) and iminodiacetonitrile (IDAN) or of β-amino nitriles. Thus, it is known that the hydrogenation of n-amino nitriles generally proceeds without problems while the hydrogenation of α-amino nitriles is associated with the occurrence of numerous disadvantages such as hydrogenolysis of the C—CN bond or the $R_2N$—C bond. "Handbook of Heterogeneous Catalytic Hydrogenation for Organic Synthesis, pages 213 to 215" indicates the problems of hydrogenation of α-amino nitriles for α-alkylamino nitriles or cyclic α-amino nitriles compared to β-amino nitriles. The known stability problems associated with α-amino nitriles are presumably the main reason why only the hydrogenation of the α-amino nitriles AAN or IDAN to EDA (ethylenediamine) or DETA (diethylenetriamine) has been described in detail to date. EDA or DETA are prepared industrially by the EDC or MEA processes described below. However, a corresponding hydrogenation is not known for higher α-amino nitriles.

DE-A 3 003 729 describes a process for the hydrogenation of aliphatic nitrites, alkyleneoxy nitrites and alkyleneamino nitrites to primary amines over a cobalt or ruthenium catalyst in the presence of a solvent system. The solvent system used comprises water and ammonia together with an ether or polyether. The alkyleneamino nitriles or alkyleneoxy nitriles which can be used as starting materials are in each case defined by means of complex general formulae. As specific compounds or examples which can be hydrogenated to the corresponding diamine, mention is made of, inter alia, ethylenediaminedipropionitrile (EDDPN; also referred to as N,N'-bis(cyanoethyl)-ethylenediamine) and 3,3'-(ethylenedioxy) dipropionitrile. DE-A 3 003 729 discloses, on the other hand, no suggestion as to the use of individual compounds of EDA derivatives having cyanomethyl substituents, e.g. EDDN or EDMN. In addition, the latter does not come under the general definition of alkyleneamino nitrites according to this document.

EP-A 0 382 508 describes a process for the batchwise preparation of acyclic, aliphatic polyamines by hydrogenation of acyclic, aliphatic polynitriles in the liquid phase over Raney cobalt catalysts, preferably in the presence of anhydrous ammonia. Here, a polynitrile solution is fed into a reaction zone comprising the Raney cobalt catalyst in an essentially oxygen-free atmosphere. During the entire reaction time, the polynitrile solution is fed in at a rate which is no greater than the maximum rate at which the polynitrile reacts with the hydrogen in the reaction zone. This process makes it possible to prepare polyamines from polynitriles such as iminodiacetonitrile (IDAN), nitrilotriacetonitrile (NTAN), ethylenediaminetetraacetonitrile (EDTN) or further compounds having 2 or more cyano groups which are not specified in more detail. The direct hydrogenation product of IDAN is diethylenetriamine (DETA).

EP-A 212 986 relates to a further process in which the same aliphatic polynitriles as in EP-A 0 382 508 can be hydrogenated to the corresponding polyamines over a granular Raney cobalt catalyst in the presence of a liquid primary or secondary amine comprised in the feed stream. As amino component which must be present, mention is made of, inter alia, ethylenediamine (EDA) together with numerous further primary or secondary amines.

EP-A 1 209 146 relates to a further process for the continuous hydrogenation of nitrites to primary amines, in which the respective nitrites are reacted in the liquid phase over a suspended, activated Raney catalyst based on an alloy of aluminum and the reaction is carried out in the absence of ammonia and basic alkali metal or alkaline earth metal compounds. Nitrites which can be converted into the corresponding ethylene amines include, among many others, IDAN, EDTN, EDDPN or ethylenediaminemono-propionitrile (EDMPN).

EP-B 0 913 388 relates to a process for the catalytic hydrogenation of nitriles, which comprises contacting of the nitrile with hydrogen in the presence of a cobalt sponge catalyst under conditions for carrying out the conversion of the nitrile group into the primary amine. The cobalt sponge catalyst has been treated beforehand with a catalytic amount of lithium hydroxide and the process is carried out in the presence of water. Suitable nitriles are aliphatic nitriles having from 1 to 30 carbon atoms, including β-amino nitrites such as dimethylaminopropionitrile. A further process for preparing polyamines from the corresponding polynitriles is disclosed in DE-A 27 55 687. In this process, the hydrogenation is carried out over a hydrogenation catalyst in pellet form in the presence of a stabilizer which inhibits decomposition of the catalyst. As polynitrile, it is possible to use, inter alia, ethylenediaminedipropionitrile (EDDPN). A suitable stabilizer is, inter alia, EDA.

US-A 2006/0041170 relates to a process for preparing TETA, in particular TETA salts, and their use as drugs. In this multistage process, EDDN is prepared first. EDDN is subsequently reacted with benzaldehyde to form a (cyclic) imidazolidine derivative. This cyclic compound, which has two cyano groups, is reduced, for example by reaction with hydrogen, to give the corresponding cyclic diamino compound. This diamino compound is in turn hydrolyzed in the presence of an acid to give the corresponding TETA salt. In an alternative embodiment, the cyclic diamino compound is likewise reacted with benzaldehyde to form the corresponding diimino compound which is subsequently again hydrolyzed in the presence of an acid to give the corresponding TETA salt. A further process alternative described in this document is reaction of EDDN with Boc protective groups (tert-butoxycarbonyl groups). The EDDN derivative protected by two Boc protective groups obtained in this way is subsequently hydrogenated to give the corresponding protected TETA derivative. The Bac protective groups are removed by acid hydrolysis to give the corresponding TETA salt. A disadvantage of this process described in US-A 2006/0041170 is, in particular, that it is a multistage hydrogenation process in which the starting material EDDN used firstly has to be chemically converted into a derivative in order to carry out the hydrogenation. A further disadvantage is that TETA is initially obtained as salt and not in the free base form.

Thus, it is disclosed nowhere in the prior art that EDDN or amino nitrile mixtures comprising EDDN and EDMN can be used for the preparation of TETA and, if appropriate, further ethylene amines by direct hydrogenation of the amino nitrile. However, other (industrial) processes for preparing TETA are known.

EP-A 222 934 relates to a process for preparing higher alkylene polyamines by reaction of a vicinal dihaloalkane with an excess of ammonia in the aqueous phase with addition of a strong base, resulting in formation of an imine intermediate which is subsequently reacted with an alkylene polyamine to form the higher alkylene polyamine. A suitable vicinal dihaloalkane is, in particular, ethylene dichloride (EDC or 1,2-dichloroethane). Alkylene polyamines used are, in particular, ethylenediamine or higher ethylene amines such as DETA and also TETA and tetraethylenepentamine (TEPA). In these processes (EDC processes), a mixture of various ethylene amines (linear ethylene amines such as EDA, DETA, TETA, TEPA or higher ethylene amines and cyclic derivatives such as piperazine (Pip) or aminoethylpiperazine (AEPip)) is obtained. Depending on which ethylene amine is added to the starting materials EDC and NH$_3$, the reaction mixture comprises a corresponding proportion of higher ethylene amities. If, for example, TEPA is to be specifically produced, the ethylene amine TETA is added to the starting materials EDC and NH$_3$. As a result, the product (ethylene amine mixture) comprises a higher proportion of TEPA, but also the above-mentioned further linear and cyclic ethylene amines. Disadvantages of this process are, in particular, that the process proceeds with a low selectivity (in respect of the components of the ethylene amine mixture obtained) and that a specific ethylene amine (for example DETA) firstly has to be prepared and is subsequently introduced into the process to produce the next higher ethylene amine (for example TETA) in a targeted manner or to increase the yield. In addition, this process presents a corrosion problem because of the starting materials used (haloalkanes) and the hydrochloric acid formed and also an environmental problem because of the salts formed.

U.S. Pat. No. 3,462,493 relates to a process for preparing TETA, in which an at least five-fold molar excess of EDA is reacted with ethylene dichloride or ethylene dibromide. By-products formed here are, in particular, Pip or piperazinoethylethylenediamine.

DE-T 689 11 508 describes an alternative process for preparing linearly extended polyalkylene polyamines such as TETA. In this process, a bifunctional aliphatic alcohol is reacted with an amine reactant in the presence of a tungsten-comprising catalyst. A suitable bifunctional aliphatic alcohol is, in particular, monoethanolamine (MEA), and EDA or DETA can, for example, be used as amine reactants. This process gives principally mixtures of linearly extended polyalkylene polyamines (i.e. ethylene amine mixtures). These ethylene amine mixtures comprise the ethylene amines DETA, TETA, TEPA, Pip, AEPip or piperazine derivatives of higher ethylene amines, with the proportion of the respective components varying as a function of the amine reactants used. If DETA is used as amine reactant, an ethylene amine mixture having a high proportion of TETA and TEPA is obtained. Disadvantages of this process are that the process proceeds with a low selectivity (in respect of the components of the ethylene amine mixture obtained) and that an additional ethylene amine has to be synthesized first and then reacted with the bifunctional aliphatic alcohol (for example MEA). This forms relatively large amounts of by-products such as aminoethylethanolamine (AEEA) or higher hydroxy-comprising ethylene amines which are of little commercial interest. The relatively large amount of by-products formed is due to MEA or the higher ethanolamines (e.g. AEEA) being able to react with themselves instead of with the amine used. Owing to the (statistically) many possible reactions, the selectivity to the linear TETA is quite low because of the coproducts and cannot be controlled. The synthesis can be carried out only at a partial conversion.

An overview of the preparation of ethylene amines is given by the SRI report "CEH Product Review Ethyleneamines", SRI International, 2003; pp. 1-53, in which EDA or DETA, in particular, are prepared by processes corresponding to those described above (using the starting materials EDC or MEA). Here, higher ethylene amines such as TETA or TEPA are formed as by-products or are obtained in higher yield by renewed reaction of the starting materials with EDA or DETA.

Furthermore, some processes for preparing EDDN or EDMN have been described in the literature. Thus, K. Masuzawa at al., Bull. Chem. Soc. Japan, volume 41 (1968), pages 702-706, describe a process for the preparation and reaction of nitrogen and sulfur analogues of 2-piperazinone derivatives. The preparation of this class of substances starts out from the starting materials EDA and FACH. The two starting materials are reacted in an equimolar ratio, using methanol as solvent. After the reaction solution has been allowed to stand at room temperature for two days, the solvent and unreacted starting materials are removed under reduced pressure to give an oily product. This oily product comprises a cyclic compound together with EDMN as secondary component. The reaction was carried out with exclusion of water. The oily product is subsequently converted in a multistage process into the desired 2-piperazinone derivatives. This document also describes the preparation of EDDN as an undesirable secondary reaction in the reaction of EDA with FACH. EDDN is obtained if a molar excess of EDA is reacted with FACH in methanol at from 55 to 60° C. After concentrating the reaction mixture under reduced pressure, the product is isolated by vacuum distillation. A yield of about 27.3% based on the EDA used is obtained here.

H. Baganz et al., Chem. Ber, 90 (1957), pages 2944-2949, describe a process for preparing N,N'-ethylenebisamino acid derivatives, with the dihydrochloride of EDDN serving as starting material for this multistage process. This document also describes a synthetic method for the dihydrochloride of EDDN. Here, the dihydrochloride of EDA and potassium cyanide (KCN) are placed in a reaction vessel and 30% strength formaldehyde is subsequently introduced dropwise into the reaction vessel, with the reaction temperature not exceeding 25° C. After a reaction time of 12 hours and addition of sodium hydroxide, the product is shaken with ether, dried and precipitated as ammonium salt by addition of hydrogen chloride. The product obtained is subsequently crystallized. A disadvantage of this process is, in particular, the use of hydrogen chloride and KCN, which give the aqueous phase a high salt content. Furthermore, the extraction with ether is problematical since, owing to the good solubility of EDDN in water, the reaction product does not go completely into the ether phase.

H. Brown et al., Helvetica Chimica Acta, volume 43 (1960), pages 659-666, describe a process for preparing complexing agents of the thiazole series. This multistage process uses EDDN as starting material, and this document also comprises a synthetic method for preparing EDDN. According to the process described therein, EDA and water are placed in a reaction apparatus and HCN and calcium cyanide ($Ca(CN)_2$) in water are subsequently added simultaneously while stirring and cooling in ice. However, no formaldehyde is used in this process. After a complicated work-up, EDDN is obtained in a relatively low yield.

The abovementioned US-A 2006/0041170 likewise comprises methods of preparing the starting material EDDN described therein. Firstly, EDDN can be prepared by direct alkylation of EDA by means of a haloacetonitrile such as chloroacetonitrile or bromoacetonitrile. Secondly, EDDN is prepared by the above-described reaction of EDA, in particular the dihydrochloride of EDA, firstly with formaldehyde and subsequently with cyano salts such as KCN. The reaction product obtained is then treated with an acid. If EDA is used as starting material, it is firstly converted into its salt form, in particular into the dihydrochloride, before being reacted further with formaldehyde. A disadvantage of this process is the salt formation caused by the use of cyano salts. A further disadvantage is the handling of solid EDA salts, since EDA is either used directly as salt or is firstly converted into a salt. In addition, the process described in US-A 2006/0041170 is not suitable for continuous operation.

BRIEF SUMMARY OF THE INVENTION

It is therefore an object of the present invention to provide a simple and inexpensive process for preparing TETA and, if appropriate, further ethylene amines in targeted amounts.

The object is achieved by a process for preparing triethylenetetramine (TETA), which, comprises the following steps:
a) reaction of ethylenediamine (EDA) with formaldehyde and hydrocyanic acid (HCN) in a molar ratio of EDA to formaldehyde to HCN of from 1:1.5:1.5 to 1:2:2 to give ethylenediaminediacetonitrile (EDON),
b) hydrogenation of the EDDN obtained in step a) in the presence of a catalyst and a solvent.

DETAILED DESCRIPTOIN OF THE INVENTION

The process of the invention has the advantage that TETA and, if appropriate, the further main component DETA can be prepared with a high conversion and/or selectivity. The increased selectivity is reflected, in particular, in the EDDN used being hydrogenated predominantly to TETA. The by-products formed are mainly further linear ethylene amines. The proportion of cyclic ethylene amines is relatively low in the process of the invention. However, some of the further ethylene amines are likewise interesting products of value (mainly the linear ethylene amines such as DETA) whose isolation is worthwhile, for example in industrial processes.

On the other hand, cyclic ethylene amines such as AEPip are of relatively little interest as product of value but can be reused by recirculation.

The selectivity of the process of the invention can be advantageously increased by separating off low boilers, in particular hydrocyanic acid (HCN), before the hydrogenation. The hydrocyanic acid can also occur as decomposition product of formaldehyde cyanohydrin (FACH). Hydrocyanic acid in particular can act as catalyst poison in the hydrogenation.

When the low boilers have been separated off, EDDN and if appropriate further amino nitrites such as EDMN or DETDN can be prepared more quickly and with higher selectivity. This also has a positive effect on the selectivity in the subsequent hydrogenation.

EDDN and if appropriate EDMN are advantageously reacted quantitatively or virtually quantitatively. This is particularly important in industrial processes since unreacted starting material generally has to be recirculated to the production circuit or disposed of. Processes in which relatively large amounts of EDDN and/or EDMN are not reacted are particularly disadvantageous because of the high instability of the EDDN or EDMN. Firstly, both EDDN and EDMN tend to decompose at elevated temperatures so that the decomposition products cannot be recirculated to the respective circuit; secondly, this decomposition can also proceed with explosive force. Since the amino nitriles can be reacted completely in the process of the invention, no efforts have to be made in respect of recirculation to the production cycle.

A further advantage of the process of the invention is that, in contrast to EDC processes, it is not necessary to use chlorinated hydrocarbons as starting material. In addition, no hydrochloric acid or salts thereof are obtained as further reaction product. The disposal of the abovementioned materials is an (environmental) problem, particularly in industrial processes. An advantage over the MEA process is that, owing to the different starting materials, the formation of AEEA and further compounds having a hydroxy function does not play any role. Another advantage is that the process of the invention can be carried out continuously.

If an amino nitrile mixture is hydrogenated in the process of the invention, it is advantageous that, depending on market requirements, a higher or lower proportion of TETA or DETA can be prepared. This is based on the fact that the ratio of the starting materials EDMN to EDDN is in principle reflected in the product in respect of DETA to TETA. Thus, specific amino nitrite mixture compositions can be used in a targeted manner in the process of the invention in order to obtain the ratios desired by the market. The process of the invention gives, with high selectivity, an ethylene amine mixture which comprises at least 30% of TETA together with at least 5% of DETA and possibly further ethylene amines such as piperazine derivatives as products of value.

Owing to step a), the process of the invention has the further advantage that EDDN and also, if appropriate, a targeted mixture comprising EDDN and further amino nitrites such as EDMN can be prepared in a simple manner and in high purity. Both EDDN and, if appropriate, EDMN can be isolated in a simple manner in the form of pure crystals, while the processes of the prior art give the product as a viscous liquid from which the desired product can be isolated only by means of complicated work-up steps and in poor purity.

A further advantage of the process of the invention is that cyano salts such as KCN and $Ca(CN)_2$ can be dispensed with. In addition, EDA is advantageously used not as salt but in the form of the free base as starting material in the process of the invention. Consequently, the proportion of salts in the reaction solution is lower in the process of the invention and a smaller amount of salt-comprising by-products or unreacted starting materials are thus obtained. This is particularly advantageous in industrial processes. A high salt content in the reaction solution is particularly disadvantageous when the process of the invention is carried out in an aqueous phase. The desired product can consequently be prepared in a simple manner by means of fewer reaction steps. Furthermore, it is advantageous that the process of the invention, in particular step a), can be carried out continuously.

A further important advantage of the process of the invention is that an ethylene amine mixture which comprises two (main) products (TETA and DETA) in ratios which can be set in a targeted manner can be prepared from only one starting material (EDA). In a further embodiment of the present invention, the DETA comprised in the ethylene mixture can be recirculated in its entirety or in part to step a) in order to react it with, preferably, FACH. DETDN and/or DETMN are prepared in this way and are subsequently hydrogenated further to give TEPA and/or TETA. The various ethylene amines TEPA, TETA and DETA can consequently be prepared by the process of the invention from one starting material (EDA) with partial recirculation of the hydrogenation product DETA. Depending on the starting conditions chosen, it is possible to prepare ethylene amine mixtures in which the abovementioned main products are present in variable ratios to one another, with the individual ethylene amines (TETA, TEPA and/or DETA and also possibly further by-products) being able to be isolated from the ethylene amine mixture.

In a further embodiment, recirculation of the AEPip formed as cyclic by-product in the hydrogenation to step a) is also conceivable. The conversion of AEPip into the corresponding amino nitriles and subsequent hydrogenation gives diaminoethylpiperazine (DAEPip), piperazinoethylethylenediamine (PEEDA) and aminoethylpiperazinylethylethylenediamine (AEPEEDA). These cyclic ethylene amines are likewise of interest as products of value.

Step a)

In step a), ethylenediamine (EDA) is reacted with formaldehyde and hydrocyanic acid (HCN) in a molar ratio of EDA to formaldehyde to HCN of from 1:1.5:1.5 to 1:2:2 to give ethylenediaminediacetonitrile (EDDN).

Unless indicated otherwise below (option a1) to a4)), the starting components of step a) can be introduced into the respective reaction vessel in any order. For example, all of one starting material can be initially placed in the reaction vessel and a second starting material can be added. EDDN can advantageously be prepared according to one of the options a1) to a4) described below. EDDN is particularly preferably prepared according to optional).

According to optional), formaldehyde and HCN are firstly reacted to form formaldehyde cyanohydrin (FACH), and EDA is subsequently reacted with FACH in a molar ratio of EDA to FACH of from 1:1.5 to 1:2. EDA, formaldehyde and HCN are commercially available products or can in principle be prepared by methods known to those skilled in the art. In the process of the invention, EDA is preferably used in the form of the free base, but salts such as the dihydrochloride of EDA can, if appropriate, also be used as starting materials.

The reaction of formaldehyde and HCN is known to those skilled in the art. FACH can be prepared by reaction of aqueous formaldehyde with hydrocyanic acid. Formaldehyde is preferably present as a 30-50% strength aqueous solution, and hydrocyanic acid is preferably used in a purity of from 90 to 100%. This reaction is preferably carried out at a pH of 5.5, which is preferably set by means of sodium hydroxide or ammonia. The reaction can be carried out at temperatures of from 20 to 70° C., for example in a loop reactor and/or tube reactor.

Instead of using purified hydrocyanic acid (HCN), crude HCN gas can also be chemisorbed in aqueous formaldehyde solution under the abovementioned conditions to give FACH. The crude HCN gas is preferably prepared by pyrolysis of formamide and comprises water and, in particular, small proportions of ammonia.

If appropriate, the aqueous FACH solution obtained can be concentrated and freed of low boilers, in particular hydrocyanic acid, by vacuum evaporation under mild conditions, for example using a falling film evaporator or thin film evaporator. It is preferably concentrated to a 50-80% strength FACH solution. Before the concentration step, it is advantageous to stabilize the FACH solution by reducing the pH to $\leq 4$, preferably to $\leq 3$, for example by addition of acid, e.g. by addition of phosphoric acid or preferably sulfuric acid.

The molar ratio of EDA to FACH in optional) is preferably from about 1:1.8 to 1:2, in particular about 1:2.

According to option a2), EDDN is prepared by reaction of an ethylenediamine-formaldehyde adduct (EDFA) with hydrocyanic acid (HCN) in a molar ratio of EDFA to HCN of from 1:1.5 to 1:2. The molar ratio of EDFA to HCN is preferably from 1:1.8 to 1:2, in particular about 1:2. EDFA is preferably prepared by mixing of approximately equimolar amounts of EDA and formaldehyde.

According to option a3), EDA is reacted with a mixture of formaldehyde and hydrocyanic acid (GFB) in a molar ratio of EDA to GFB of from 1:1.5 to 1:2. The molar ratio of EDA to GFB is preferably from 1:1.8 to 1:2, in particular about 1:2. The GFB is preferably prepared by mixing of approximately equimolar amounts of formaldehyde and hydrocyanic acid.

According to option a4), EDA is reacted simultaneously (in parallel) with formaldehyde and hydrocyanic acid (HCN) in a molar ratio of EDA to formaldehyde to HCN of from 1:1.5:1.5 to 1:2:2. The molar ratio of EDA to formaldehyde to HCN is preferably from 1:1.8:1.8 to 1:2:2, in particular about 1:2:2. In this embodiment, the three starting components are preferably introduced into the reaction vessel simultaneously or stepwise in equal molar portions based on the total amount of the respective starting materials.

The respective starting materials or intermediates can sometimes be used in the process of the invention immediately after their preparation. For example, in option a1), FACH can be used as starting material in the process of the invention without prior isolation. However, FACH can, if appropriate, be isolated first after its preparation and subsequently be used in the process of the invention.

In an embodiment of the present invention, step a) is carried out in the absence of or at least largely in the absence of cyano salts such as KCN.

Step a) of the process of the invention is normally carried out in the presence of a solvent. In the process of the invention for preparing EDDN, the starting materials are preferably reacted in an aqueous phase. Apart from water, it is possible, if appropriate, to use further solvents which are known to those skilled in the art and are miscible with water. However, alcohols, in particular methanol, are less preferably used as solvents.

Step a) is preferably carried out at a temperature of from 10 to 90° C., in particular from 30 to 70° C. The reaction can be carried out at atmospheric pressure or, if appropriate, at superatmospheric pressure. Step a) is preferably carried out in a tube reactor or a cascade of stirred vessels. Step a) can preferably also be carried out as a continuous process, in particular as an industrial process.

In step a) of the process of the invention, ethylenediaminemonoacetonitrile (EDMN) is obtained as an important by-product in addition to the main product EDDN. The process of the invention can be controlled by choice of the respective process parameters (for example starting material, temperature, solvent or pressure) so that the proportion of EDMN in the reaction product varies and EDMN is obtained not as by-product but as second main reaction product. In this embodiment of the present invention, an amino nitrile mixture comprising both EDDN and EDMN (as main product) is thus prepared. In this case, amino nitrile mixtures comprising at least 30% by weight of EDON and at least 5% by weight of EDMN are preferably prepared. EDDN is normally comprised in the amino nitrile mixture in a proportion of from 30 to 95% by weight, preferably from 50 to 95% by weight, particularly preferably from 75 to 90% by weight. The amino nitrile mixture normally comprises EDMN in a proportion of from 5 to 70% by weight, preferably from 5 to 50% by weight, particularly preferably from 10 to 25% by weight. The above values are based only on the ratio of EDDN to EDMN without taking account of further amino nitriles which have been formed by the recirculation of hydrogenation products from step b).

The above percentages by weight of EDDN and EDMN are based on the total amount of amino nitriles comprised in the mixture. Water or other solvents which are additionally present are not taken into account in these percentages.

An increase in the proportion of EDMN in the amino nitrile mixture is preferably achieved by using a relatively low molar proportion of FACH (optional)), HCN (option a2)), GFB (option a3)) or formaldehyde and HCN (option a4)) within the respective parameter ranges indicated for the options a1)-a4). Thus, for example, a molar ratio of EDA to FACH of from 1:1.5 to 1:1.8 is used according to option a) in order to increase the proportion of EDMN.

Furthermore, an amino nitrile mixture comprising a relatively low proportion of EDMN, for example 510% by weight, in particular from 5 to 10% by weight, can, in one embodiment of the present invention, be prepared by reaction of EDA with a very high molar proportion of FACH. Here, an aqueous solution comprising 40% by weight of FACH or pure FACH is preferably used. The molar ratio of EDA to FACH is in this case preferably 1:2.

If appropriate, very pure EDDN having a low proportion of EDMN can also be prepared according to the present invention. The content of EDMN and any further by-products, for example other amino nitriles, is preferably 10% by weight, in particular 5% by weight, based on EDDN.

Step b)

Step b) comprises the hydrogenation of the EDDN obtained in step a) in the presence of a catalyst and a solvent. For the purposes of the present invention, hydrogenation means the reaction of EDDN and, if appropriate, EDMN and any further amino nitriles present with hydrogen.

Step b) can be carried out directly after step a), or one or more of the purification steps indicated below can, if appropriate, be carried out between step a) and step b).

i) Low Boiler Removal

In an embodiment of the present invention, the low boilers are separated off from the reaction product from step a) before the hydrogenation. If FACH is used to prepare EDDN and, if appropriate, EDMN, the low boiler removal can be carried out before the reaction of FACH with EDA.

Preference is given to separating off hydrocyanic acid (HCN) as low boiler. HCN can also occur as decomposition product of FACH. Furthermore, any ammonia present can be separated off at this point. The removal is preferably effected by distillation, for example in a thin film evaporation such as a Sambay distillation ("Chemie Ingenieur Technik, Vol. 27, pp. 257-261). If appropriate, the reaction mixture can also be stripped by means of nitrogen.

ii) Reduction of the Water Content Water can be completely or partly removed either preferably together with the low boilers or after the low boiler removal. The water is preferably removed by distillation. This can be effected in one or more stages in an evaporator or a cascade of evaporators, with different pressures or temperatures being able to be set from stage to stage. The water removal can also be carried out in a distillation column. The water removal is preferably carried out under reduced pressure. The remaining amino nitrile or amino nitrile mixture can still comprise residual water and low boilers. Preference is given to a residual water content of at least 10% by weight. The low boilers are then comprised only in small traces. It is also conceivable for the low boiler removal and water removal to be carried out after the FACH synthesis.

iii) Adsorption of Impurities

The amino nitrile (mixture) obtained in step a) can be purified by adsorption of impurities on an adsorbent, e.g. activated carbon or an ion exchanger, either directly or after low boiler removal or after removal of low boilers and water. This can be carried out, for example, in an adsorption column filled with the adsorbent.

EDDN is a solid at room temperature, as is EDMN. Consequently, step b) of the process of the invention is carried out in the presence of a solvent such as an organic solvent and/or water. Preference is given to using water as solvent, and it is also possible, if appropriate, to use mixtures of water and organic solvents such as ethers, in particular THF. However, the additional use of an organic solvent (inert organic compound) in addition to water has been found to be advantageous since stabilization of the individual components of the aqueous amino nitrile mixture, in particular in the presence of the resulting amines, can be achieved by use of an organic solvent. In addition, the use of organic solvents enables a flushing effect (reduction in the flushing cycles, reduction of the discharge of catalyst) on the catalyst used to be achieved, as a result of which its operating life is increased or its consumption is reduced (longer catalyst life) and the space velocity over the catalyst can be improved. Furthermore, the use of suitable solvents can reduce the formation of further by-products such as AEPip.

A suitable solvent which can comprise one or more components should preferably have the following properties;
(a) the solvent should have a stabilizing effect on EDDN or, if appropriate, EDMN, in particular prevent their decomposition at the prevailing temperatures;
(b) the solvent should display a good solvent capability for hydrogen;
(c) the solvent should be inert under the reaction conditions;
(d) the reaction mixture (EDDN or, if appropriate, EDMN, if appropriate water and solvent) should form a single phase under the reaction conditions;
(e) the choice of solvent should be made with a view to a preferred separation of the product from the product stream by distillation subsequent to the hydrogenation, preferably avoiding a separation which is energy-intensive or complicated in terms of apparatus (e.g. close-boiling mixtures or azeotropes which are difficult to separate);
(f) the solvent should readily be able to be separated off from the products, i.e. the boiling point should be sufficiently different from those of the products, with preference being given to a boiling point lower than those of the products.

Possible solvents (apart from water) are organic solvents, for example amides such as N-methylpyrrolidone (NMP) and dimethylformamide (DMF), aromatic and aliphatic hydrocarbons such as benzene and xylene, alcohols such as methanol, ethanol, propanol, isopropanol, butanol, isobutanol, secondary butanol and tertiary butanol, amines, esters such as methyl acetate or ethyl acetate and ethers such as diisopropyl ether, diisobutyl ether, glycol dimethyl ether, diglycol dimethyl ether, dioxane and tetrahydrofuran (THF). Preference is given to using ethers, more preferably cyclic ethers and particularly preferably tetrahydrofuran, in the process of the invention. In a further preferred embodiment, alcohols, in particular methanol, are used as organic solvent.

The solvent is used in a weight ratio to the amino nitrile used (EDDN and, if appropriate, EDMN) of from 0.1:1 to 15:1. The concentration of the amino nitrile mixture in the solution in which the hydrogenation is carried out should be selected so that a suitable feed rate or residence time can be set. Preference is given to mixing from 10 to 50% by weight of the amino nitrile with the solvent. Based on the particularly preferred solvents methanol and tetrahydrofuran, it is advantageous, for example, to use the amino nitrile in an amount of from 20 to 40% by weight based on the solvent.

If water is present, the proportion of water in the solution is in the range from 0 to 60% by weight, preferably from 10 to 30% by weight. The percentages indicated for the water are based on the amino nitrile mixture.

If appropriate, the solution in which the hydrogenation is carried out can comprise additional additives. Possible additives are in principle hydroxides such as alkali metal hydroxides, alkoxides, amides, amines. Amines, particularly EDA and ammonia, in particular EDA, are preferred as additives. Furthermore, acidic additives such as silicates can additionally be comprised in the solution. These substances can be added as pure substance or as a solution in a solvent. The process of the invention is preferably carried out with addition of additives.

In an embodiment of the process, no ammonia is added to the solution in which the hydrogenation is carried out. If ammonia is present in solution in the starting materials or in any aqueous solution used or is liberated as by-product in the hydrogenation, this does not cause any problems. Any ammonia present can be removed by methods known to those skilled in the art, for example by distillation. If ammonia is dispensed with, this has the advantage that the autogenous pressure of the system is reduced.

As catalysts for the hydrogenation of the nitrile function to the amine, it is possible to use catalysts which comprise one or more elements of transition group 8 of the Periodic Table (Fe, Co, Ni, Ru, Rh, Pd, Os, Ir, Pt), preferably Fe, Co, Ni, Ru or Rh, particularly preferably Co or Ni, as active species. These include skeletal catalysts (also referred to as Raney® type; hereinafter also: Raney catalyst) which are obtained by leaching (activation) of an alloy of a hydrogenation-active metal and a further component (preferably Al). The catalysts can additionally comprise one or more promoters. In a preferred embodiment, Raney catalysts, preferably Raney cobalt or Raney nickel catalysts and particularly preferably Raney cobalt catalysts doped with at least one of the elements Cr, Ni or Fe or Raney nickel catalysts doped with one of the elements Mo, Cr or Fe, are used in the process of the invention.

The catalysts can be used as all-active catalysts or in supported form. Supports used are preferably metal oxides such as $Al_2O_3$, $SiO_2$, $ZrO_2$, $TiO_2$, mixtures of metal oxides or carbon (activated carbons, carbon blacks, graphite).

The oxidic catalysts are activated outside the reactor or in the reactor by reduction of the metal oxides in a hydrogen-comprising gas stream at elevated temperature before use. If the catalysts are reduced outside the reactor, this can be followed by passivation by means of an oxygen-comprising gas stream or embedding in an inert material in order to avoid uncontrolled oxidation in air and to make safe handling possible. As inert material, it is possible to use organic solvents such as alcohols or else water or an amine, preferably the reaction product. The skeletal catalysts are an exception in the activation; these can be activated by leaching with aqueous base, as described, for example, in EP-A 1 209 146.

Depending on the process carried out (suspension hydrogenation, fluidized-bed process, fixed-bed hydrogenation), the catalysts are used as powder, crushed material or shaped bodies (preferably extrudates or pellets).

Particularly preferred fixed-bed catalysts are the all-active cobalt catalysts doped with Mn, P and alkali metal (Li, Na, K, Rb, Cs) which are disclosed in EP-A 742 045. The catalytically active composition of these catalysts before reduction with hydrogen comprises from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, in each case calculated as oxide.

Further suitable catalysts are the catalysts disclosed in EP-A 963 975, whose catalytically active composition before treatment with hydrogen comprises from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO, with the molar ratio of Ni:Cu being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ or $MnO_2$, and no oxygen-comprising compounds of molybdenum, for example the catalyst A disclosed in this document which has the composition 33% by weight of Zr, calculated as $ZrO_2$, 28% by weight of Ni, calculated as NiO, 11% by weight of Cu, calculated as CuO, and 28% by weight of Co, calculated as CoO.

Further suitable catalysts are the catalysts disclosed in EP-A 696 572 whose catalytically active composition before reduction with hydrogen comprises from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ or $MnO_2$, for example the catalyst specifically disclosed in this document which has the composition 31.5% by weight of $ZrO_2$, 50% by weight of NiO, 17% by weight of CuO and 1.5% by weight of $MoO_3$. The catalysts described in WO-A 99/44984 which comprise (a) iron or a compound based on iron or mixtures thereof, (b) from 0.001 to 0.3% by weight, based on (a), of a promoter based on 2, 3, 4 or 5 elements selected from the group consisting of Al, Si, Zr, Ti, V, (c) from 0 to 0.3% by weight, based on (a), of a compound based on an alkali metal and/or alkaline earth metal and (d) from 0.001 to 1% by weight, based on (a), of manganese are likewise suitable.

In suspension processes, preference is given to using Raney catalysts. In Raney catalysts, the active catalyst is produced as "metal sponge" from a binary alloy (nickel, iron, cobalt with aluminum or silicon) by leaching of one component by means of acid or alkali. Residues of the original alloying partner often act synergistically.

The Raney catalysts used in the process of the invention are preferably produced from an alloy of cobalt or nickel, particularly preferably cobalt, and a further alloying component which is soluble in alkalis. Aluminum is preferably used as this soluble alloying component, but it is also possible to use other components such as zinc and silicon or mixtures of such components.

To activate the Raney catalyst, the soluble alloying component is extracted completely or partly by means of alkali, for example aqueous sodium hydroxide. The catalyst can then be washed, for example, with water or organic solvents.

One or more further elements can be present as promoters in the catalyst. Examples of promoters are metals of transition groups IB, VIB and/or VIII of the Periodic Table, e.g. chromium, iron, molybdenum, nickel, copper, etc.

The activation of the catalysts by leaching of the soluble component (typically aluminum) can be carried out either in the reactor itself or before introduction into the reactor. The preactivated catalysts are air-sensitive and pyrophoric and are therefore generally stored and handled under a medium such as water, an organic solvent or a substance which is present in the reaction carried out according to the invention (solvent, starting material, product) or embedded in an organic compound which is solid at room temperature.

In a preferred embodiment, use is made according to the invention of a skeletal Raney cobalt catalyst which has been obtained from a Co/Al alloy by leaching with aqueous alkali metal hydroxide solution, e.g. sodium hydroxide, and subsequent washing with water and preferably comprises at least one of the elements Fe, Ni or Cr as promoters.

Such catalysts typically comprise cobalt together with from 1 to 30% by weight of Al, preferably from 2 to 12% by weight of Al, very particularly preferably from 3 to 6% by weight of Al, from 0 to 10% by weight of Cr, preferably from 0.1 to 7% by weight of Cr, very particularly preferably from 0.5 to 5% by weight of Cr, in particular from 1.5 to 3.5% by weight of Cr, from 0 to 10% by weight of Fe, preferably from 0.1 to 3% by weight of Fe, very particularly preferably from 0.2 to 1% by weight of Fe, and/or from 0 to 10% by weight of Ni, preferably from 0.1 to 7% by weight of Ni, very particularly preferably from 0.5 to 5% by weight of Ni, in particular from 1 to 4% by weight of Ni, with the percentages by weight being based in each case on the total weight of the catalyst.

It can, for example, be advantageous to use a skeletal cobalt catalyst "Raney 2724" from W.R. Grace & Co. as catalyst in the process of the invention. This catalyst has the following composition:

Al: from 2 to 6% by weight, Co: ≧86% by weight, Fe: from 0 to 1% by weight, Ni: from 1 to 4% by weight, Cr: from 1.5 to 3.5% by weight.

According to the invention, it is likewise possible to use a skeletal nickel catalyst which has been obtained from an Ni/Al alloy by leaching with aqueous alkali metal hydroxide solution, e.g. sodium hydroxide, and subsequent washing with water and preferably comprises at least one of the elements Fe, Cr as promoters.

Such catalysts typically comprise nickel together with
from 1 to 30% by weight of Al, preferably from 2 to 20% by weight of Al, very particularly preferably from 5 to 14% by weight of Al,
from 0 to 10% by weight of Cr, preferably from 0.1 to 7% by weight of Cr, very particularly preferably from 1 to 4% by weight of Cr, and/or
from 0 to 10% by weight of Fe, preferably from 0.1 to 7% by weight of Fe, very particularly preferably from 1 to 4% by weight of Fe, with the percentages by weight being based in each case on the total weight of the catalyst.

It can be advantageous to use, for example, a skeletal nickel catalyst A 4000 from Johnson Matthey as catalyst in the process of the invention. This catalyst has the following composition:

Al: ≦14% by weight, Ni: ≧80% by weight, Fe: from 1 to 4% by weight, Cr: from 1 to 4% by weight.

When the activity and/or selectivity of the catalysts decreases, they can, if appropriate, be regenerated by methods known to those skilled in the art, as disclosed, for example, in WO 99/33561 and the documents cited therein.

The regeneration of the catalyst can be carried out in the actual reactor (in situ) or on the catalyst after removal from the reactor (ex situ). In fixed-bed processes, the catalyst is preferably regenerated in situ, while in the case of suspension processes, preference is given to continuously or discontinuously taking out part of the catalyst, regenerating it ex situ and returning it to the reactor.

The temperatures at which step b) is carried out are in the range from 40 to 150° C., preferably from 70 to 140° C., in particular from 80 to 140° C.

The pressure prevailing in the hydrogenation is generally from 5 to 300 bar, preferably from 30 to 250 bar, particularly preferably from 40 to 160 bar.

In a preferred embodiment, EDDN or the amino nitrile mixture comprising EDDN is fed to the hydrogenation at a rate which is no greater than the rate at which EDDN and, if appropriate, the other components of the amino nitrile mixture react with hydrogen in the hydrogenation.

The feed rate is thus preferably set so that an effectively quantitative conversion is achieved. This is influenced by temperature, pressure, type of mixture, amount and type of the catalyst, of the reaction medium, quality of mixing of the contents of the reactor, residence time, etc.

A solvent (or a plurality of solvents) is/are used in the process of the invention, with the solvent firstly being mixed with EDDN or the amino nitrile mixture. The solution obtained, which may, if appropriate, also comprise additives, is subsequently fed into the catalyst-comprising reaction vessel. If appropriate, for example in semibatch processes, part of the solvent can be initially placed in the reaction vessel together with the catalyst, after which the solution is metered in. In continuous processes, a partial amount of the solvent can also be introduced into the reaction vessel separately from the solution comprising EDDN, the solvent and, if appropriate, the additive. In a preferred embodiment, the EDDN comprised in the solution and any further amino nitriles such as EDMN comprised are fed in at a rate which is no greater than the rate at which EDDN reacts with hydrogen in the hydrogenation. If appropriate, for example, in semibatch processes, part of the solvent can be initially placed in the reaction vessel together with the catalyst, after which the solution is metered in.

The process of the invention for preparing TETA by hydrogenation of EDDN can be carried out continuously, semicontinuously or batchwise in a fixed-bed, fluidized-bed or suspension mode in customary reaction vessels suitable for the catalysis. Suitable reaction vessels for carrying out the hydrogenation are ones in which contacting of the amino nitrile and the catalyst with the gaseous hydrogen under superatmospheric pressure is possible.

The hydrogenation in the suspension mode can be carried out in a stirred reactor, jet loop reactor, jet nozzle reactor, bubble column reactor or in a cascade of identical or different reactors of this type. In the case of hydrogenation over a fixed-bed catalyst, tube reactors and shell-and-tube reactors are conceivable.

In the case of a fixed-bed catalyst, the amino nitrile is passed over the catalyst in the upflow mode or downflow mode. However, preference is given to using the suspension mode in semicontinuous or preferably continuous operation.

The hydrogenation of the nitrile groups takes place with liberation of heat which generally has to be removed. The removal of heat can be effected by means of built-in heat-exchange surfaces, cooling jackets or external heat exchangers in a circuit around the reactor. The hydrogenation reactor or a cascade of hydrogenation reactors can be operated in a single pass. As an alternative, it is also possible to employ a recycle mode of operation, in which part of the output from the reactor is recirculated to the reactor inlet, preferably without prior work-up of the recycle stream. Optimum dilution of the reaction solution can be achieved in this way. In particular, the recycle stream can be cooled in a simple and inexpensive way by means of an external heat exchanger and the heat of reaction can thus be removed. The reactor can also be operated adiabatically in this way, with the temperature rise of the reaction solution being able to be limited by means of the cooled recycle stream. Since the reactor itself then does not have to be cooled, a simple and inexpensive construction is possible. An alternative is a cooled shell-and-tube reactor (only in the case of a fixed bed). A combination of the two modes of operation is also conceivable. Here, preference is given to installing a fixed-bed reactor downstream of a suspension reactor.

The process of the invention gives the linear ethylene amine ($C_6$ product) TETA as main product (1st case) and further ethylene amines as secondary components. If an amino nitrile mixture comprising EDDN and EDMN is used in the process of the invention, an ethylene amine mixture which comprises the two linear ethylene amines ($C_6$ product and $C_4$ product) TETA and DETA as main component (2nd case) and further ethylene amines as secondary components is obtained.

The secondary components can in both cases be both linear and cyclic ethylene amines or other by-products. An important cyclic by-product formed in the 1st case is AEPip ($C_6$ (by-)product). The ratio of TETA to AEPip in the product is normally in the range from 3:1 to 12:1. This ratio can, for example, be controlled by choice of the solvent, the catalyst and/or the addition of an additive. In the 1st case, DETA is likewise a (linear) by-product. Further secondary reactions which take place are decomposition reactions, but these can be controlled and minimized by, in particular, the choice of solvent, the addition rate, the starting material purity and/or catalyst. In the 2nd case, Pip occurs as further important cyclic by-product ($C_4$ (by-)product), which is formed mainly from EDMN. With regard to the formation and control of the ratio of DETA to Pip, what has been said in respect of TETA to AEPip applies. The process of the invention is illustrated in the following scheme 1 for the 2nd case in which EDDN and EDMN are prepared jointly, for example starting from FACH.

Scheme 1

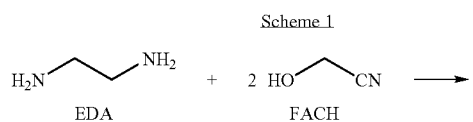

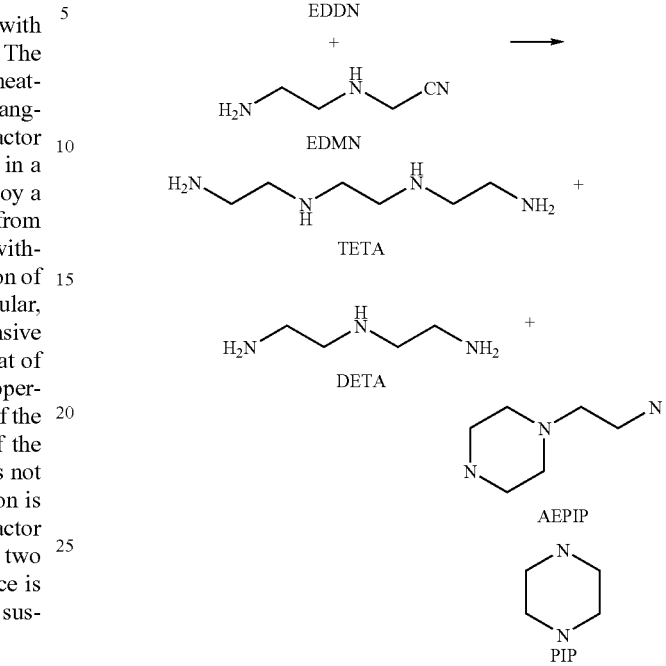

In the second case, the term "ethylene amine mixture" is used because the reaction product comprises two linear ethylene amines as main components (TETA and DETA), while in the first case only one linear ethylene amine is present as main product (TETA). The by-products mentioned above or below are consequently not taken into account in the definition of terms in these two cases.

In the first case, TETA is obtained with a selectivity of preferably ≧70% by weight, in particular ≧85% by weight, based on the amount of EDDN used. In the second case, the ratio of the starting materials EDDN and EDMN is in principle reflected in that of the corresponding products TETA and DETA after the hydrogenation.

For the purposes of the present invention, the expression "further ethylene amine" refers to any hydrocarbon-comprising compound which is different from TETA (1st case) and from TETA and DETA (2nd case) and comprises at least two ethylene units and at least two functional groups selected from among primary, secondary and tertiary amino groups. The expression further ethylene amine also encompasses, for the purposes of the present invention, cyclic compounds such as piperazine (Pip) and its derivatives. Likewise, ethylene diamine (EDA) is to be considered to be a further ethylene amine. Further ethylene amines are, in particular, diethylenetriamine (DETA; only in the 1st case), piperazine (Pip), aminoethylenepiperazine (AEPip) or tetraethylenepentamine (TEPA).

In an embodiment of the present invention, the DETA obtained in the hydrogenation is recirculated in its entirety or in part to step a). This embodiment is preferably carried out in conjunction with the above-described second case in which an ethylene amine mixture comprising TETA and DETA as main components is obtained. Thus, recirculation to step a) means that DETA is used for preparing amino nitrites, in particular DETDN, which are once again subsequently hydrogenated.

DETA is preferably recirculated (in its entirety or in part) so that it is reacted with FACH according to optional). The reaction of DETA with FACH can in this case be carried out simultaneously with the reaction of EDA and FACH. As an alternative, the recirculation of DETA can also be carried out so that a partial amount of the FACH used is reacted with DETA and another partial amount is reacted with EDA.

The reaction of DETA with FACH produces mainly the amino nitrile diethylene-triaminediacetonitrile (DETDN). The reaction conditions of DETA with FACH correspond largely to the reaction conditions indicated above for the reaction of EDA with FACH. The molar ratio of DETA to FACH is preferably from 1:1.5 to 1:2. DETDN has hitherto not been described in the literature. The applicant of the present application has at the same time filed a further application which relates to a process for the preparation and hydrogenation of DETDN. The preparation of DETDN enables diethylenetriaminemonoacetonitrile (DETMN) to be additionally formed as by-product. Depending on the molar ratio of DETA to FACH, amino nitrile mixtures comprising DETDN and DETMN are produced. When only a small excess of FACH over DETA is employed, more DETMN than DETDN is formed.

The amino nitrile mixture comprising DETDN and, if appropriate, DETMN which has been prepared by reaction of DETA with FACH is subsequently combined with the jointly or if appropriate separately synthesized EDDN, which may, if appropriate, also comprise EDMN, and hydrogenated (if DETA and EDA have been reacted separately with FACH).

In the subsequent hydrogenation of this embodiment of the process of the invention, in which not only EDDN and EDMN but also DETDN and, if appropriate, DETMN are hydrogenated jointly, an ethylene amine mixture comprising TETA and DETA as main components and also TEPA is obtained. It may be pointed out at this juncture that TETA is also formed from DETMN in the hydrogenation. The presence of EDMN in the hydrogenation is necessary to enable the DETA formed to be recirculated again either in its entirety or in part. Scheme 2 below gives an overview of this embodiment of the process of the invention in respect of the substep of reaction of DETA with FACH. The parallel preparation and hydrogenation of EDDN and EDMN is not shown in this scheme.

which are in turn subsequently hydrogenated to give cyclic ethylene amines (piperazine derivatives of higher ethylene amines).

Preference is given to recirculating AEPip (in its entirety or in part) so that it is reacted with FACH according to optional). The reaction of AEPip with FACH can here be carried out simultaneously with the reaction of EDA and/or DETA with FACH. As an alternative, the recirculation of AEPip can also be carried out so that a partial amount of the FACH used is reacted with AEPip and further partial amounts are reacted with EDA and/or DETA.

The reaction of AEPip with FACH produces mainly the cyclic amino nitriles piperazinyl-ethylaminoacetonitrile (PEAN), aminoethylpiperazinylacetonitrile (AEPAN) and/or cyanomethylpiperazinylethylaminoacetonitrile (CMPEAN). The reaction conditions for the reaction of AEPip with FACH correspond in principle to the reaction conditions indicated above for the reaction of DETA with FACH. The molar ratio of AEPip to FACH is preferably from 1:1.5 to 1:2.

The cyclic amino nitrites PEAN, AEPAN and CMPEAN formed in the reaction of AEPip with FACH are new compounds which have not yet been described in the literature. Accordingly, these 3 cyclic amino nitrites as such or a mixture thereof and processes for preparing them are additionally provided by the present invention.

The amino nitrile mixture comprising PEAN, AEPAN and/or CMPEAN prepared by reaction of AEPip with EACH is subsequently combined with the separately synthesized EDDN, which can, if appropriate, also comprise EDMN, and/or the separately synthesized DETDN, which can, if appropriate, also comprise DETMN, and hydrogenated (if AEPip and DETA and/or EDA have been reacted separately with FACH).

In the subsequent hydrogenation of this embodiment of the process of the invention, in which not only EDDN and EDMN but also DETDN, PEAN, AEPAN and/or CMPEAN and, if appropriate, DETMN are hydrogenated jointly, an ethylene amine mixture comprising TETA and DETA as main components and also TEPA, diamino-ethylpiperazine (DAEPip), piperazinoethylethylenediamine (PEEDA) and/or aminoethyl-piperazinoethylethylenediamine (AEPEEDA) is obtained. The presence of EDMN in the hydrogenation is Scheme 2

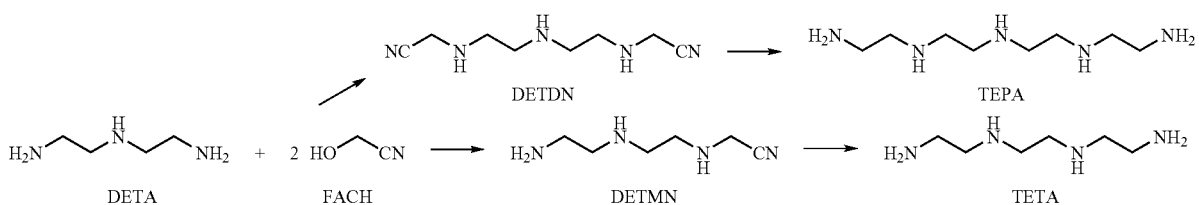

In a further embodiment of the present invention, the AEPip obtained as by-product in the hydrogenation is recirculated in its entirety or in part to step a). This embodiment is preferably carried out in conjunction with the above-described second case in which an ethylene amine mixture comprising TETA and DETA as main components is obtained. The recirculation can be effected either together with or separately from the above-described recirculation of DETA. The recirculation of AEPip is preferably carried out together with that of DETA. Recirculation to step a) thus means that AEPip is used for preparing cyclic amino nitriles necessary only to produce DETDN and from it TEPA as further main component from the recirculated DETA. Scheme 3 below gives an overview of this embodiment of the process of the invention in respect of the substep of reaction of AEPip with FACH. The parallel preparation and hydrogenation of EDDN and EDMN or DETDN and DETMN is not shown in this scheme. The cyclic ethylene amines AEPEEDA, DAEPip and PEEDA are known by-products in the industrial preparation of TETA or TEPA by the EDC process. Preferred cyclic ethylene amines in this embodiment are DAEPip and PEEDA.

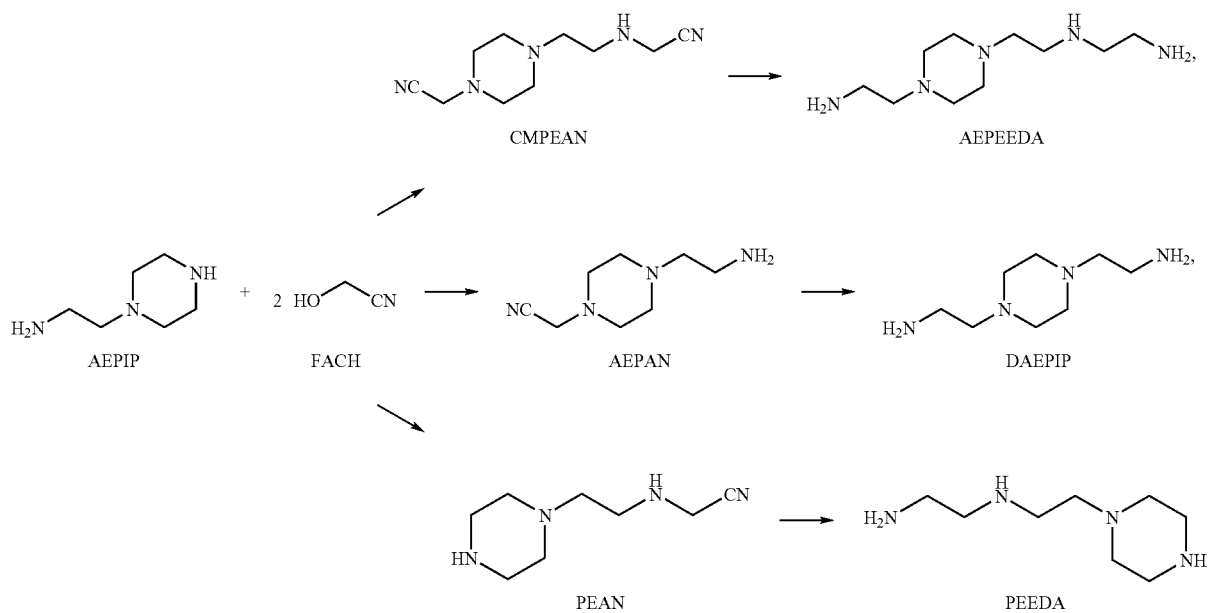

Scheme 3

After the hydrogenation, the product obtained (TETA or ethylene amine mixture) can, if appropriate, be purified further, for example by separating off the solvent and/or the catalyst by methods known to those skilled in the art. In particular, the main products (TETA and, if appropriate, DETA, TEPA or, if appropriate, the cyclic ethylene amines DAEPip, PEEDA and/or AEPEEDA) can be isolated from the reaction product either jointly or individually by methods known to those skilled in the art. If the respective main products are isolated jointly, for example by means of distillation, they can subsequently be separated into the respective individual products. Thus, pure TETA, pure DETA, pure TEPA and, if appropriate, pure DAEPip, pure PEEDA and/or pure AEPEEDA are ultimately obtained. Other impurities, by-products or further ethylene amines such as TEPA or Pip can, if they are present, likewise be separated off from the respective product by methods known to those skilled in the art.

If appropriate, mixtures of 2 or more of the abovementioned ethylene amines can also be isolated, for example as mixtures comprising TETA and/or TEPA.

In a preferred embodiment, the process of the invention is carried out using tetrahydrofuran or methanol as solvent. The temperature in the hydrogenation is preferably from 80 to 140° C., and the pressure is preferably from 40 to 160 bar. The hydrogenation is preferably carried out in the presence of EDA and/or, if appropriate, ammonia.

The process of the invention gives not only high total yields of ethylene amines but also a high proportion of linear TETA or further linear ethylene amines.

The following examples illustrate the process of the invention. The proportions are in % by weight unless indicated otherwise. An internal standard, viz. diethylene glycol dimethyl ether (DEGDME), included in the process allows quantification of the product by determination of any volatile decomposition products formed. Quantification is carried out by means of gas chromatography (GC), with methanol being added to the samples taken in each case in order to effect homogenization.

EXAMPLES

General Method for the Synthesis of Formaldehyde Cyanohydrin (FACH)

Variant a)

6000 g (60 mol) of formaldehyde (30%) are placed in a 6 l reaction vessel provided with a propeller stirrer and a pH of 5.5 is set by means of sodium hydroxide solution (1 mol/l). 1661 g (61.2 mol) of hydrocyanic acid are metered in gaseous form via a heated U-tube which is located below the stirrer over a period of 2.5 hours, with the reaction temperature being maintained at 30° C. and the pH being maintained at 5.5. After a further stirring time of 30 minutes, the pH is set to 2.5 by means of sulfuric acid (50% strength). The respective content is determined by means of Liebig titration.

Variant b)

7000 g (70 mol) of formaldehyde (30%) are placed in a 6 l reaction vessel provided with a propeller stirrer and a pH of 5.5 is set by means of sodium hydroxide solution (1 mol/l). 1938 g (71.4 mal) of hydrocyanic acid are metered in gaseous form via a U-tube which has been heated to 50° C. and is located below the stirrer over, a period of 3 hours, with the reaction temperature being maintained at 30° C. and the pH being maintained at 5.5. After a further stirring time of 10 minutes, the pH is set to 2.5 by means of sulfuric acid (50% strength). To separate off low boilers, in particular hydrocyanic acid, the reaction product mixture is subjected to a Sambay distillation (as described in "Chemie Ingenieur Technik, Vol. 27, pp. 257-261) (1 mbar, 30° C.). The respective content is determined by means of Liebig titration and set, if appropriate, to a content of 43-44% or 67% of FACH by addition of water.

Example 1

Formaldehyde Cyanohydrin

FACH is prepared according to variant a) of the general method.

Ethylenediaminediacetonitrile 536.5 g (4 mol) of FACH (42.5%) are placed in a 2 l reaction vessel and, while cooling in ice, 132 g (2.2 mol) of ethylenediamine are added dropwise at a temperature of not more than 35° C. over a period of 2 hours. The reaction mixture changes color from slightly yellowish via orange to brown. After stirring for a further short time, the free hydrocyanic acid is removed by stripping with nitrogen (Volhard titration). According to Liebig titration, a conversion of FACH of 97.2% is obtained.

Triethylenetetramine a) The product obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture composed of 13.8 g of the crude EDDN solution, 13.8 g of an internal standard and 4.2 g of water in 106 g of THF is metered in over a period of 120 minutes. The reaction mixture is stirred under the reaction conditions for a further 60 minutes. The product mixture is homogenized by means of methanol. The selectivity is 28% of AEPip and 30% of TETA. In addition, 4% by weight of C4 products (Pip+DETA) are found.

b) The same product is likewise hydrogenated in a semibatch process. Here, 3.25 g of a Cr-doped Raney cobalt catalyst and also 15 ml of THF and 5.4 g of EDA are placed in a 270 ml autoclave. The autoclave is heated to 120° C. and pressurized with hydrogen to a total pressure of 100 bar. A mixture composed of 13.8 g of the crude EDDN solution, 13.8 g of an internal standard and 4.2 g of water in 106 g of THF is metered in over a period of 120 minutes. The reaction mixture is stirred under the reaction conditions for a further 60 minutes. The product mixture is homogenized by means of methanol. The selectivity is 12% of AEPip and 43% of TETA. In addition, 4% by weight of C4 products (Pip+DETA) were found.

Comparison with Example 1a shows a positive influence of EDA on TETA formation.

Example 2

Formaldehyde Cyanohydrin

FACH is prepared according to variant b) of the general method.

Ethylenediaminediacetonitrile 132 g (2.2 mol) of EDA are placed in a 2 l reaction vessel and, while cooling in ice, 511.2 g (4 mol) of FACH (44.6%) are added dropwise at a temperature of not more than 30° C. over a period of 2 hours. After stirring for another 4.5 hours, the slightly yellowish solution is dispensed. The conversion of FACH according to Liebig titration is 99.2%. The reaction mixture comprises 0.11% of free hydrocyanic acid (determined by Volhard titration). Titration indicates an EDDN yield of 91.7% based on FACH used. EDMN cannot be determined by titration. On the assumption that EDMN is formed from reacted ethylenediamine which does not react to form EDDN, the total amino nitrile yield is 95.7% and the yield of EDMN is thus 4%.

Triethylenetetramine a) The product obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture composed of 13.8 g of the crude EDDN solution, 13.8 g of an internal standard and 4.2 g of water in 106 g of THF is metered in over a period of 120 minutes. The reaction mixture is stirred under the reaction conditions for a further 60 minutes. The product mixture is homogenized by means of methanol. The selectivity is 27% of AEPip and 47% of TETA. In addition, 8% by weight of C4 products are detected.

It can be seen that the removal of low boilers after the FACH synthesis enables a significantly better yield of ethylene amines to be achieved. The excess of EDA in the EDDN synthesis results in formation of EDMN which is hydrogenated to the C4 products DETA and Pip.

b) The same product is likewise hydrogenated in a semibatch process. Here, 3.25 g of a Cr-doped Raney cobalt catalyst and also 15 ml of THF and 13.5 g of EDA are placed in a 270 ml autoclave. The autoclave is heated to 120° C. and pressurized with hydrogen to a total pressure of 100 bar. A mixture composed of 13.8 g of the crude EDDN solution, 13.8 g of an internal standard and 4.2 g of water in 106 g of THF is metered in over a period of 120 minutes. The reaction mixture is stirred under the reaction conditions for a further 60 minutes. The product mixture is homogenized by means of methanol. The selectivity is 8% of AEPip and 82% of TETA. In addition, 16% by weight of C4 products are detected.

The addition of EDA in variant 2b) results in formation of more linear TETA. There is likewise an increase in C4 products, which is due to EDA condensation. In the reported percentage by weight of $C_4$ products, the increase in weight caused by EDA condensation is taken into account.

Example 3

Formaldehyde Cyanohydrin

FACH is prepared according to variant b) of the general method.

Ethylenediaminediacetonitrile 132 g (2.2 mol) of EDA are placed in a 2 l reaction vessel and, while cooling in ice, 340.8 g (4 mol) of FACH (67%) are added dropwise at a temperature of not more than 30° C. over a period of about 2 hours. After stirring for another 3 hours, the yellowish solution is dispensed. The conversion of FACH according to Liebig titration is 99.5%. The reaction mixture comprises 0.08% of free hydrocyanic acid (determined by Volhard titration). Titration indicates an EDDN yield of 82.9% based on FACH used. EDMN cannot be determined by titration. On the assumption that EDMN is formed from reacted ethylenediamine which does not react to form EDDN, the total amino nitrile yield is 90.5% and the yield of EDMN is thus 8%.

Triethylenetetramine a) The product obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture composed of 13.8 g of the crude EDDN solution, 13.8 g of an internal standard and 10 g of water in 106 g of THF is metered in over a period of 120 minutes. The reaction mixture is stirred under the reaction conditions for a further 60 minutes. The product mixture is homogenized by means of methanol. The selectivity is 10% of AEPip and 69% of TETA. In addition, 13% of C4 products (Pip and DETA) are obtained.

More water than in Example 2a is added for comparability. The excess of EDA in the EDDN synthesis results in formation of EDMN which is hydrogenated to the C4 products DETA and Pip.

b) The product obtained is hydrogenated in a semibatch process. Here, 3.25 g of a Cr-doped Raney cobalt catalyst, 15 ml of THF and 13.5 g of EDA are placed in a 270 ml autoclave. The autoclave is heated to 120° C. and pressurized with hydrogen to a total pressure of 100 bar. A mixture composed of 13.8 g of the crude EDDN solution, 13.8 g of an internal standard and 10 g of water in 106 g of THF is metered in over a period of 120 minutes. The reaction mixture is stirred under the reaction conditions for a further 60 minutes. The product mixture is homogenized by means of methanol. The selectivity is 5% of AEPip and 76% of TETA. In addition, 16% of C4 products are obtained.

The addition of EDA results in formation of more linear TETA. There is likewise an increase in C4 products, which is due to EDA condensation.

c) The product obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture composed of 13.8 g of the crude EDDN solution and 13.8 g of an internal standard in 106 g of THF is metered in over a period of 120 minutes. The reaction mixture is stirred under the reaction conditions for a further 60 minutes. The product mixture is homogenized by means of methanol. The selectivity is 9% of AEPip and 76% of TETA. In addition, 12% of C4 products (Pip and DETA) are obtained.

Compared to Example 3a, additional addition of water is dispensed with, which has a positive effect on TETA.

Example 4

Formaldehyde Cyanohydrin

FACH is prepared according to variant b) of the general method.

Ethylenediaminediacetonitrile 132 g (2.2 mol) of EDA are placed in a 2 l reaction vessel and, while cooling in ice, 340.8 g (4 mol) of FACH (67%) are added dropwise at a temperature of not more than 50° C. over a period of 35 minutes. After stirring for another 1 hour, the virtually clear solution is dispensed. The conversion of FACH according to Liebig titration is 99.2%. The reaction mixture comprises 0.07% of free hydrocyanic acid (determined by Volhard titration). Titration indicates an EDDN yield of 87.7% based on FACH used. EDMN cannot be determined by titration. On the assumption that EDMN is formed from reacted ethylenediamine which does not react to form EDDN, the total amino nitrile yield is 93% and the yield of EDMN is thus 5%.

Triethylenetetramine a) The product obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture composed of 13.8 g of the crude EDDN solution and 13.8 g of an internal standard in 106 g of THF is metered in over a period of 120 minutes. The reaction mixture is stirred under the reaction conditions for a further 60 minutes. The product mixture is homogenized by means of methanol. The selectivity is 10% of AEPip and 76% of TETA. In addition, 11% of C4 products (Pip and DETA) are obtained.

Experiment 4a confirms the results of 3c. Here too, the yield of C4 products (DETA and Pip) is about 11% due to the excess of EDA in the EDDN synthesis, b) The product obtained is hydrogenated in a semibatch process. Here, 3.25 g of a Cr-doped Raney cobalt catalyst, 15 ml of THF and 13.5 g of EDA are placed in a 270 ml autoclave. The autoclave is heated to 120° C. and pressurized with hydrogen to a total pressure of 100 bar. A mixture composed of 13.8 g of the crude EDDN solution and 13.8 g of an internal standard in 106 g of THF is metered in over a period of 120 minutes. The reaction mixture is stirred under the reaction conditions for a further 60 minutes. The product mixture is homogenized by means of methanol. The selectivity is 4% of AEPip and 80% of TETA. In addition, 15% of C4 products are obtained.

Example 4b confirms that the formation of AEPip can be substantially suppressed by carrying out the hydrogenation in the presence of EDA and a smaller amount of water. The content of 15% by weight of C4 products is usual in the case of the present EDA excess in the EDDN synthesis and EDA in the hydrogenation.

Example 5

Formaldehyde Cyanohydrin

FACH is prepared according to variant b) of the general method.

Ethylenediaminediacetonitrile 180 g (3 mol) of EDA are placed in a 2 l reaction vessel and, while cooling in ice, 511.2 g (6 mol) of FACH (67%) are added dropwise at a temperature of not more than 50° C. over a period of about 1 hour. After stirring for another 1.5 hours, the light yellow solution is dispensed. The conversion of FACH according to Liebig titration is 99.2%. The reaction mixture comprises 0.02% of free hydrocyanic acid (determined by Volhard titration). Titration indicates an EDDN yield of 92.6% based on FACH used. EDMN cannot be determined by titration. On the assumption that EDMN is formed from reacted ethylenediamine which does not react to form EDDN, the total amino nitrile yield is 94.5% and the yield of EDMN is thus 2%.

Triethylenetetramine a) The product obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture composed of 13.8 g of the crude EDDN solution and 13.8 g of an internal standard in 106 g of THF is metered in over a period of 120 minutes. The reaction mixture is stirred under the reaction conditions for a further 60 minutes. The product mixture is homogenized by means of methanol. The selectivity is 10% of AEPip and 77% of TETA. In addition, 3% of C4 products (Pip and DETA) are obtained.

It can be seen that the use of half-molar amounts of EDA in the preparation of EDDN results in a content of C4 products after the hydrogenation of only 3%.

b) The product obtained is hydrogenated in a semibatch process. Here, 3.25 g of a Cr-doped Raney cobalt catalyst, 15 ml of THF and 13.5 g of EDA are placed in a 270 ml autoclave. The autoclave is heated to 120° C. and pressurized with hydrogen to a total pressure of 100 bar. A mixture composed of 13.8 g of the crude EDDN solution and 13.8 g of an internal standard in 106 g of THF is metered in over a period of 120 minutes. The reaction mixture is stirred under the reaction conditions for a further 60 minutes. The product mixture is homogenized by means of methanol. The selectivity is 6% of AEPip and 82% of TETA. In addition, 7% of C4 products are obtained.

Here too, the content of C4 products is significantly below that of Example 4b.

The above examples show that the quality of the FACH used has an influence on the reaction time and the color of the product in the preparation of EDDN. In addition, a higher selectivity is achieved in the subsequent hydrogenation if the FACH is purified by distillation. Furthermore, the addition of an additive has a positive effect on the selectivity to linear ethylene amines. The amount of water likewise has an influence on the formation of linear TETA.

Example 6

Formaldehyde Cyanohydrin
FACH is prepared according to variant b) of the general method.
Ethylenediaminediacetonitrile
132 g (2.2 mol) of EDA are placed in a 2 l reaction vessel and, while cooling in ice, 340.8 g (4 mol) of FACH (67%) are added dropwise at a temperature of not more than 50° C. over a period of 35 minutes. After stirring for another 1 hour, the virtually clear solution is dispensed. The conversion of FACH according to Liebig titration is 99.2%. The reaction mixture comprises 0.07% of free hydrocyanic acid (determined by Volhard titration). Titration indicates an EDDN yield of 87.7% based on FACH used. EDMN cannot be determined by titration. On the assumption that EDMN is formed from reacted ethylenediamine which does not react to form EDDN, the total amino nitrile yield is 93% and the yield of EDMN is thus 5%.
Triethylenetetramine
The subsequent hydrogenation of the solution obtained above is carried out continuously in a 270 ml autoclave provided with baffles and disk stirrer. 22 g of Cr-doped Raney cobalt are placed in the autoclave and 20 standard l of hydrogen are fed in continuously. 4.5 g/h of the EDDN solution together with 2 g/h of an internal standard, 4.9 g/h of EDA and 30 g/h of THF are fed in. The hydrogenation is carried out at 120° C. and 100 bar. Over a period of 26 hours, an average of 2.6% by weight of Pip, 19.5% by weight of DETA as C4 products and also 5.6% by weight of AEPip and 79.9% by weight of TETA as C6 products can be isolated. Based on EDDN, this corresponds to a yield of 96% of C6 products.

Example 7

Formaldehyde Cyanohydrin
FACH is prepared according to variant b) of the general method.
Ethylenediaminediacetonitrile
120 g (2 mol) of EDA are placed in a 2 l reaction vessel and, while cooling in ice, 340.8 g (4 mol) of FACH (67%) are added dropwise at a temperature of not more than 70° C. over a period of 30 minutes. After stirring for another 1 hour, the clear yellow-orange solution is dispensed. The conversion of FACH according to Liebig titration is 99.3%. The reaction mixture comprises 0.12% of free hydrocyanic acid (determined by Volhard titration). Titration indicates an EDDN yield of 91.6% based on FACH used. EDMN cannot be determined by titration. On the assumption that EDMN is formed from reacted ethylenediamine which does not react to form EDDN, the total amino nitrile yield is 94.3% and the yield of EDMN is thus 3%.
Triethylenetetramine
The subsequent hydrogenation of the solution obtained above is carried out continuously in a 270 ml autoclave provided with baffles and disk stirrer. 22 g of Cr-doped Raney cobalt are placed in the autoclave and 20 standard l of hydrogen are fed in continuously. 4.5 g/h of the EDDN solution together with 2 g/h of an internal standard, 4.9 g/h of EDA and 30 g/h of THF are fed in. The hydrogenation is carried out at 120° C. and 100 bar. Over a period of 26 hours, an average of 2.4% by weight of Pip, 13.2% by weight of DETA as C4 products and also 4.8% by weight of AEPip and 84.1% by weight of TETA as C6 products can be isolated. Based on EDDN, this corresponds to a yield of 98% of C6 products.

Example 8

Influence of the Amount of Reactants Per Amount of Catalyst in the Hydrogenation
In a separate trial, the influence of the amount of reactants per amount of catalyst only on the ratio of TETA/AEPip is examined.
Formaldehyde Cyanohydrin
FACH is prepared according to variant a) of the general method.
Ethylenediaminediacetonitrile
132 g (2.2 mol) of EDA are placed in a 2 l reaction vessel and, while cooling in ice, 506.6 g (4 mol) of FACH (45% strength) are added dropwise at a temperature of not more than 35° C. over a period of 1.5 hours. After stirring for another 1 hour, a further 14.3 g (0.1 mol) of FACH (45% strength) is added and the mixture is heated to 40° C.
According to Liebig titration, a conversion of FACH of about 100% is obtained.
(EDDN Hydrogenation at Various Amounts of Reactants Per Amount of Catalyst):
3.25 g (dry) of a Cr-doped Raney cobalt catalyst and 15 ml of THF are placed in a 270 ml autoclave. The autoclave is heated to 120° C. and pressurized with hydrogen to a total pressure of 200 bar. 13.8 g of the aqueous EDDN solution obtained above, 13.8 g of an internal standard and 4.2 g of water in 106 g of THF are metered in over a defined period of time. The reaction mixture is stirred under the reaction conditions for a further 60 minutes. Samples are taken at different times and are homogenized by means of methanol. After the addition is complete, no EDDN can be detected.
The ratio of TETA/AEPip is determined as:

| a) | 60 min addition: | TETA/AEPip: 2.2 |
| b) | 180 min addition: | TETA/AEPip: 3.3 |
| c) | 180 min addition: | TETA/AEPip: 4.5 |

At a hydrogenation temperature of 80° C. and addition over 60 minutes, a TETA/AEPip ratio of only 1.3 can be achieved.

Example 9

Ammonia as Additive
The EDDN solution obtained in Example 7 is used for the hydrogenation in the presence of ammonia.
a) 3.25 g (dry) of a Cr-doped Raney cobalt catalyst, 15 ml of THF and 5.2 g of EDA are placed in a 270 ml autoclave. The autoclave is heated to 120° C. and pressurized with hydrogen to a total pressure of 200 bar. 13.8 g of the aqueous EDDN solution obtained above (43% by weight), 13.8 g of an internal standard and 4.2 g of water in 106 g of THF are metered in over a period of 60 minutes. The reaction mixture is stirred under the reaction conditions for a further 60 minutes. Samples are taken at different times and are homogenized by means of methanol. After the addition is complete, no EDDN can be detected. After an after-hydrogenation time of 60 minutes, the ratio of TETA to AEPip is 4.1.

In a further experiment, 12 g of ammonia are initially placed in the autoclave in addition to EDA. The ratio could be increased to 9.0 by this means.

b) 3.25 g (dry) of a Cr-doped Raney cobalt catalyst, 15 ml of THF and 12 g of ammonia are placed in a 270 ml autoclave. The autoclave is heated to 120° C. and pressurized with hydrogen to a total pressure of 200 bar. 13.8 g of the aqueous EDDN solution obtained above (43% by weight), 13.8 g of an internal standard and 4.2 g of water in 106 g of THF are metered in over a period of 60 minutes. The reaction mixture is stirred under the reaction conditions for a further 60 minutes. Samples are taken at different times and are homogenized by means of methanol. After the addition is complete, no EDDN can be detected. After an after-hydrogenation time of 60 minutes, the ratio of TETA to AEPip is 5.7.

The invention claimed is:

1. A process for preparing triethylenetetramine (TETA) which comprises the following steps:
   a) reacting ethylenediamine (EDA) with formaldehyde and hydrocyanic acid (HCN) in a molar ratio of EDA to formaldehyde to HCN of from 1:1.5:1.5 to 1:2:2 to give ethylenediaminediacetonitrile (EDDN),
   b) hydrogenating the EDDN obtained in step a) in the presence of a catalyst and a solvent.

2. The process according to claim 1, wherein step a) is carried out according to one of the options a1) to a4):
   a1) first reacting formaldehyde and HCN to form formaldehyde cyanohydrin (FACH), and subsequently reacting ethylenediamine (EDA) with FACH in a molar ratio of EDA to FACH of from 1:1.5 to 1:2, or
   a2) reacting an ethylenediamine-formaldehyde adduct (EDFA) with HCN in a molar ratio of EDFA to HCN of from 1:1.5 to 1:2, or
   a3) reacting EDA with a mixture of formaldehyde and hydrocyanic acid (GFB) in a molar ratio of EDA to GFB of from 1:1.5 to 1:2, or
   a4) reacting EDA simultaneously with formaldehyde and HCN in a molar ratio of EDA to formaldehyde to HCN of from 1:1.5:1.5 to 1:2:2.

3. The process according to claim 1, wherein step a) is carried out in an aqueous phase or at a temperature of from 10 to 90° C.

4. The process according to claim 1, wherein the EDDN is comprised in an amino nitrile mixture comprising EDDN and also ethylenediaminemono-acetonitrile (EDMN).

5. The process according to claim 2, wherein a relatively low molar proportion of FACH (option a1)), HCN (option a2)), GFB (option a3)) or formaldehyde and HCN (option a4)) within the parameter ranges indicated is used in order to increase the proportion of EDMN in the amino nitrile mixture.

6. The process according to claim 2, wherein the amino nitrile mixture comprises at least 30% by weight of EDDN and at least 5% by weight of EDMN.

7. The process according to claim 2, wherein step a) is carried out according to option a1).

8. The process according to claim 2, wherein low boilers are separated off from the reaction mixture before the hydrogenation (step b), with the low boiler removal in option a1) being able to be carried out after the preparation of FACH or the concentration of water being decreased before the hydrogenation.

9. The process according to claim 1, wherein a Raney catalyst, a Raney nickel catalyst or a Raney cobalt catalyst, in particular a skeletal Raney cobalt catalyst is used in step b).

10. A process according to claim 9, wherein a Raney catalyst, a Raney nickel catalyst or a Raney cobalt catalyst is used in step b).

11. The process according to claim 1, wherein, in step b), the solvent is water or an organic solvent, tetrahydrofuran or methanol, or the pressure is from 30 to 250 bar or the temperature is from 80° C. to 140° C.

12. The process according to claim 11, wherein the organic solvent is tetrahydrofuran or methanol.

13. The process according to claim 1, wherein TETA or diethylene-triamine (DETA) and optionally further ethylene amines which are comprised as by-products in the respective reaction product obtained are isolated after the hydrogenation.

14. The process according to claim 1, wherein the EDDN or the amino nitrile mixture is fed to the hydrogenation at a rate which is no greater than the rate at which EDDN or the amino nitrile mixture reacts with hydrogen in the hydrogenation.

15. The process according to claim 1, wherein the hydrogenation is carried out in the presence of an additive.

16. The process according to claim 1, wherein DETA obtained in step b) is recirculated in its entirety or in part to step a).

17. The process according to claim 2, wherein DETA obtained in step b) is recirculated in its entirety or in part to step a) and the recirculated DETA is reacted with FACH according to option a1) and the reaction product obtained is hydrogenated.

18. The process according to claim 16, wherein tetraethylenepentamine (TEPA) is isolated from the reaction product after the hydrogenation.

19. The process according to claim 1, wherein the aminoethylpiperazine (AEPip) obtained in step b) is recirculated in its entirety or in part to step a).

20. The process according to claim 2, wherein the aminoethylpiperazine (AEPip) obtained in step b) is recirculated in its entirety or in part to step a) and the recirculated AEPip is reacted with FACH according to option a1) and the reaction product obtained is hydrogenated.

21. The process according to claim 19, wherein diaminoethylpiperazine (DAEPip), piperazinoethylethylenediamine (PEEDA) or aminoethylpiperazinylethylethylenediamine (AEPEEDA) are isolated separately from the reaction product after the hydrogenation.

22. An amino nitrile selected from among piperazinylethylaminoacetonitrile (PEAN), aminoethylpiperazinylacetonitrile (AEPAN) and cyanomethylpiperazinylethylaminoacetonitrile (CMPEAN).

23. A process for preparing an amino nitrile according to claim 22, which comprises reacting AEPip with FACH.

* * * * *